US011672876B2

United States Patent
Dreher et al.

(10) Patent No.: US 11,672,876 B2
(45) Date of Patent: Jun. 13, 2023

(54) IMAGEABLE EMBOLIC MICROSPHERE

(71) Applicants: Biocompatibles UK Limited, Surrey (GB); THE UNITED STATES OF AMERICA, as represented by the Secretary Department of Health and Human Service, Bethesda, MD (US)

(72) Inventors: Matthew R. Dreher, West Conshohocken, PA (US); Bradford J. Wood, Bethesda, MD (US); Ayele H. Negussie, Bethesda, MD (US); Andrew Lennard Lewis, Surrey (GB); Yiqing Tang, Surrey (GB)

(73) Assignees: BIOCOMPATIBLES UK LIMITED, Farnham (GB); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 208 days.

(21) Appl. No.: 16/749,370

(22) Filed: Jan. 22, 2020

(65) Prior Publication Data

US 2020/0155711 A1 May 21, 2020

Related U.S. Application Data

(63) Continuation of application No. 16/381,204, filed on Apr. 11, 2019, now abandoned, which is a
(Continued)

(51) Int. Cl.
*A61K 9/00* (2006.01)
*A61K 49/04* (2006.01)
(Continued)

(52) U.S. Cl.
CPC ...... *A61K 49/0442* (2013.01); *A61K 49/0438* (2013.01); *A61K 49/0476* (2013.01);
(Continued)

(58) Field of Classification Search
CPC .................................................. A61K 49/0042
See application file for complete search history.

(56) References Cited

U.S. PATENT DOCUMENTS 2,860,986 A 11/1958 Smith
3,840,482 A 10/1974 Bolto et al.
(Continued)

FOREIGN PATENT DOCUMENTS

CN 102844054 A 12/2012
EP 0391741 A2 10/1990
(Continued)

OTHER PUBLICATIONS

Horak, Hydrogels in endovascular embolization III. Radiopaque spherical particles, their preparation and properties. Biomaterials, 8(2), 142-145. (Year: 1987).*
(Continued)

*Primary Examiner* — Paul W Dickinson
(74) *Attorney, Agent, or Firm* — Seager,Tufte & Wickhem, LLP

(57) ABSTRACT

This invention concerns imageable, radiopaque embolic beads, which are particularly useful for monitoring embolization procedures. The beads comprise iodine containing compounds which are covalently incorporated into the polymer network of a preformed hydrogel bead. The beads are prepared by activating pre-formed hydrogel beads towards nucleophilic attack and then covalently attaching iodinated compounds into the polymer network. The radiopaque beads may be loaded with chemotherapeutic agents and used in methods of embolizing hyperplastic tissue or solid tumors.

19 Claims, 6 Drawing Sheets

Related U.S. Application Data continuation of application No. 14/777,168, filed as application No. PCT/US2014/027395 on Mar. 14, 2014, now Pat. No. 10,307,493.

(60) Provisional application No. 61/790,373, filed on Mar. 15, 2013.

(51) Int. Cl.
  *C08F 116/06* (2006.01)
  *C08L 29/04* (2006.01)
  *B82Y 5/00* (2011.01)

(52) U.S. Cl.
  CPC ........ *A61K 49/0485* (2013.01); *C08F 116/06* (2013.01); *C08L 29/04* (2013.01); *B82Y 5/00* (2013.01)

(56) References Cited

U.S. PATENT DOCUMENTS

| | | |
|---|---|---|
| 4,306,031 A | 12/1981 | Itagaki et al. |
| 4,350,773 A | 9/1982 | Itagaki et al. |
| 4,406,878 A | 9/1983 | DeBoer |
| 5,330,739 A | 7/1994 | Illig |
| 5,508,317 A | 4/1996 | Muller |
| 5,558,857 A | 9/1996 | Klaveness et al. |
| 2001/0051670 A1 | 12/2001 | Goupil et al. |
| 2003/0059371 A1 | 3/2003 | Matson et al. |
| 2004/0161466 A1 | 8/2004 | Lewis et al. |
| 2009/0098207 A1 | 4/2009 | Malakhov et al. |
| 2009/0169471 A1 | 7/2009 | Richard et al. |
| 2009/0191183 A1 | 7/2009 | Gant et al. |
| 2010/0262182 A1 | 10/2010 | Moszner et al. |
| 2012/0082733 A1 | 4/2012 | Rodriguez et al. |

FOREIGN PATENT DOCUMENTS

| | | |
|---|---|---|
| EP | 1810698 A1 | 7/2007 |
| EP | 2090592 A1 | 8/2009 |
| JP | H0656676 B | 3/1994 |
| JP | 2003527402 A | 9/2003 |
| JP | 2004532182 A | 10/2004 |
| JP | 2006515358 A | 5/2006 |
| JP | 2006298904 A | 11/2006 |
| JP | 2010502814 A | 1/2010 |
| JP | 2012510535 A | 5/2012 |
| JP | 6506230 B2 | 4/2019 |
| WO | 2004071495 A1 | 8/2004 |
| WO | 2006055690 A2 | 5/2006 |
| WO | 2008039827 A2 | 4/2008 |
| WO | 2008051291 A2 | 5/2008 |
| WO | 2008059835 A1 | 5/2008 |
| WO | 2008141059 A2 | 11/2008 |
| WO | 2009132234 A2 | 10/2009 |
| WO | 2009134344 A1 | 11/2009 |
| WO | 2011084465 A2 | 7/2011 |
| WO | 2011110589 A1 | 9/2011 |
| WO | 2011135150 A1 | 11/2011 |
| WO | 2012077776 A1 | 6/2012 |
| WO | 2014151885 A1 | 9/2014 |

OTHER PUBLICATIONS

Jayakrishnan, A., et al., "Microspheres for Endovascular Embolization." In Microspheres, Microcapsules Liposomes—The MML Series ISSN 1461-1732, vol. 2 Medical Biotechnology Applications—Chapeter, Arshady, R., editor. (London: Citrus Books), pp. 92-129 (1999).

Negussie, et al., "Synthesis and characterization of image-able polyvinyl alcohol microspheres for image-guided chemoembolization," Journal of Materials Science: Materials in Medicine, vol. 26, Article No. 198 (2015).

Fuchs, Katrin, et al., "Drug-Eluting Beads Loaded with Antiangiogenic Agents for Chemoembolization: In Vitro Sunitinib Loading and Release and In Vivo Pharmacokinetics in an Animal Model," J. Vasc. Interv. Radiol., vol. 25, pp. 379-387 (2014).

Ghatalia, Pooja et al., "Hepatotoxicity with vascular endothelial growth factor receptor tyrosine kinase inhibitors: A meta-analysis of randomized clinical trials," Critical Reviews in Oncology/Hematology, vol. 93, pp. 257-276 (2015).

Hsu, Chiun et al., "Vandetanib in patients with inoperable hepatocellular carcinoma: A phase II, randomized, double-blind, placebo-controlled study," Journal of Hepatology, vol. 56, pp. 1097-1103 (2012).

Inoue, Kinya et al., "Vandetanib, an Inhibitor of VEGF Receptor-2 and EGF Receptor, Suppresses Tumor Development and Improves Prognosis of Liver Cancer in Mice," Clin. Cancer Res., pp. 1-42 (2012).

Mawad, Damia et al., "Synthesis and Characterization of Radiopaque Iodine-containing Degradable PVA Hydrogels," Biomacromolecules, vol. 9, No. 1, pp. 263-268 (2008).

McConway, M.G. et al., "Application of solid-phase antibodies to radioimmunoassay, Evaluation of two polymeric microparticles, Dynospheres * and nylon, activated by carbonyldiimidazole ortresyl chloride," Journal of Immunological Methods, vol. 95, pp. 259-266 (1986).

Millan, Jose Luis et al., "Highly Sensitive Solid-Phase Immunoenzymometric Assay for Placental and Placental-Like Alkaline Phosphatases with a Monoclonal Antibody and Monodisperse Polymer Particles," Clinical Chemistry, vol. 31, No. 1, pp. 54-59 (1985).

Pistel, Karin Frauke et al., "Brush-like branched biodegradable polyesters, part III Protein release from microspheres of poly(vinyl alcohol)-graft-poly(D,L-lactic-co-glycolic acid)," Journal of Controlled Release, vol. 73, pp. 7-20 (2001).

Sharma, Karun V., "Development of 'Imageable' Beads for Transcatheter Embolotherapy," J. Vasc. Interv. Radiol., vol. 21, pp. 865-876 (2010).

Thanoo, B. Chithambara et al., "Preparation and Properties of Barium Sulphate and Methyl Iothalamate Loaded Poly (vinyl Alcohol) Microspheres as Radiopaque Particulate Emboli," Journal of Applied Biomaterials, vol. 2, pp. 67-72 (1991).

Tsochatzis, Emmanuel A et al., "Transarterial chemoemolization and bland embolization for hepatocellular carcinoma," World Journal of Gastroenterology, vol. 20, Issue 12, pp. 3069-3077 (2014).

Wu, Jian-Bing et al., "Efficacy of Transcatheter Arterial Chemoembolization (TACE) combined with sorafenib in the treatment of advanced hepatocellular carcinoma," African Journal of Pharmacy and Pharmacology, vol. 7, No. 34, pp. 2515-2519 (2012).

* cited by examiner

Figure 4A
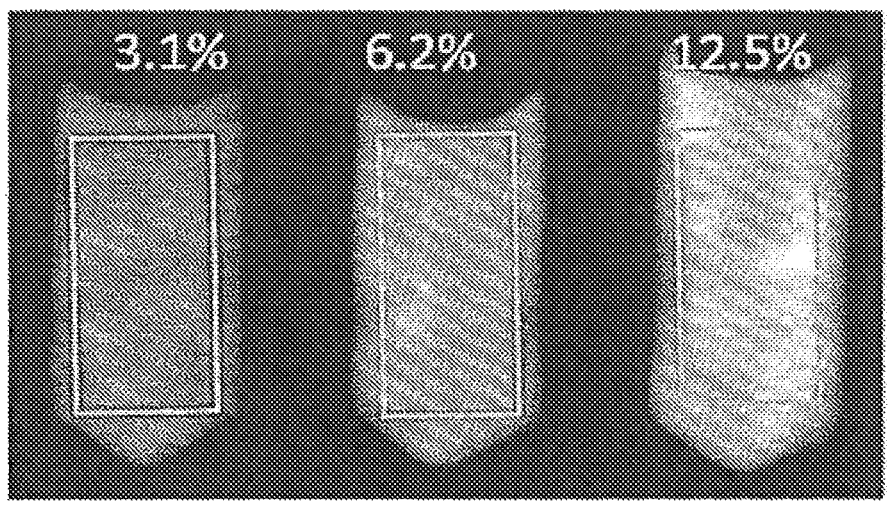
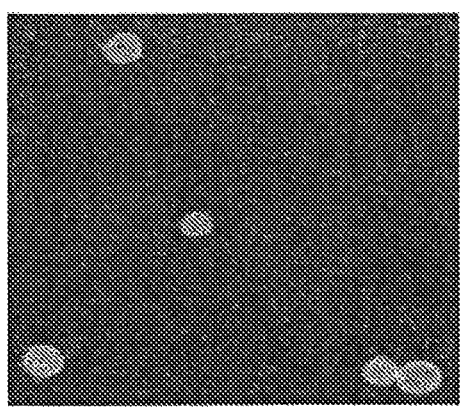 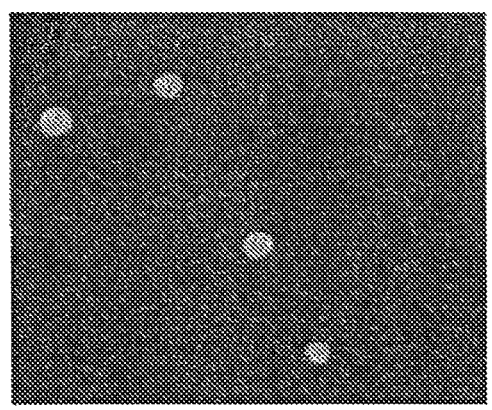
Figure 4B    Figure 4C

IMAGEABLE EMBOLIC MICROSPHERE

This application is a continuation of Ser. No. 16/381,204, filed Apr. 11, 2019, which is a continuation of U.S. patent application Ser. No. 14/777,168, filed Sep. 15, 2015, now granted as U.S. Pat. No. 10,307,493, which is a national stage filing International Application No. PCT/US2014/027395, filed on Mar. 14, 2014, and claims the benefit of priority to U.S. Provisional Application Ser. No. 61/790,373, filed Mar. 15, 2013, all of which are herein incorporated herein by reference in their entirety.

This invention relates to imageable embolic microspheres and, in particular, microspheres which are radiopaque i.e. have the property of blocking or attenuating radiation, such as X-rays. The microspheres have particularly useful radiological properties and may be used to enhance X-ray pictures in real-time, or near real-time, during medical procedures. The imageable microspheres find particular use in embolization of blood vessels, without the requirement for additional contrast agent to be added. Furthermore, the imageable microspheres can be loaded with therapeutic agents to provide localized drug delivery at the point of embolization, making them particularly useful for chemoembolization procedures.

Embolic microspheres (or beads) are useful for a variety of applications, such as occluding blood vessels and other vessels, such as fallopian tubes, filling aneurysm sacs, as arterial sealants and as puncture sealants. Embolization of blood vessels is performed for a number of reasons, e.g. to reduce blood flow to and encourage atrophy of tumors, for example in the liver, to reduce blood flow and induce atrophy of uterine fibroids, for treatment of vascular malformations, such as arteriovenous malformations (AVMs) and arteriovenous fistulas (AVFs), to seal endoleaks into aneurysm sacs, to stop uncontrolled bleeding, or to slow bleeding prior to surgery.

Chemoembolization, or chemoembolotherapy, refers to the combination of providing mechanical blockage and highly localized, in situ, delivery of therapeutic agents, commonly chemotherapeutic drugs. In the treatment of solid tumors, the chemotherapeutic agent acts as an adjunct to the embolization. This is particularly advantageous in that drug is delivered directly to the tumor whilst minimizing systemic exposure to the drug.

Whilst chemoembolization has been demonstrated to be effective in terms of improving survival rates, one drawback of the procedure is the difficulty in visualizing, in real time, the administration of the drug-loaded microspheres to ensure precise delivery at the target site. The ability to visualize an embolic particle is important not only in terms of monitoring injection and deposition of the embolic to the vascular site but is very useful for clinical follow-up to monitor the effects of embolization and ensure embolic and drug remain in the desired location and to identify regions at risk for further treatment.

Radiopacity is generally provided by using inherently radiopaque embolic materials or by mixing non-radiopaque embolic particles with radiopaque materials.

Iodinated polyvinyl alcohol (I-PVA) is a radiopaque embolic material in the form of a viscous liquid which precipitates in aqueous conditions such as those encountered in vivo. However, embolization with precipitating liquid is not reproducible and there is always a risk of precipitation occurring in an undesired location outside the target area.

Contrast agents are inherently radiopaque. Common contrast agents include ethiodized oils, such as Ethiodol® (Guerbet Joint Stock Company, France; marketed in the EU under the trade name Lipiodol®). Ethiodol is an iodinated oily X-ray contrast medium composed of about 40% iodinated poppy-seed oil (40% Iodine by weight).

Ethiodol® may be used directly as an embolization agent. Due to its viscous nature, the ethiodized oil tends to accumulate in the capillary bed and slow down blood flow. It has thus been described as "microembolic". However, such use is contraindicated by the FDA and, in any event, it fails to provide a reproducible level of embolization. As a result, embolization with ethiodized oil is normally followed by conventional embolization with particles or microspheres.

Contrast agents, such as Ethiodo®, are, however, routinely mixed with embolic particles to impart radiopacity to an injectable composition. However, such compositions tend to be unstable because of the different physical properties of the aqueous suspension of embolic particle and the oily contrast agent. This means that the injectable composition needs to be prepared immediately prior to injection. Even after administration, however, it is the contrast agent which is visible rather than the embolic particle and the contrast agent and the embolic particle may not reside at the same location in tissue.

EP1810698 describes a process for forming stable radiopaque embolic beads in which PVA hydrogel embolic beads are loaded with iodinated oils to make them radiopaque. The process described in EP1810698 requires the beads to be dry or dried for loading with iodinated oil before recovering oil-loaded beads from any excess extraparticulate loading liquid, swelling the beads in an aqueous storage liquid and sterilizing the beads by heating to a temperature of at least 90° C.

In the process of EP1810698 it is an essential step that the final product is sterilized by a heating process in the presence of water. Sterilization is carried out by heating to a suitably raised temperature of at least 90° but preferably to a higher temperature than 100° C. under pressure. It is disclosed that the radiopaque oil is not adversely affected under the preferred sterilization conditions of reduced pressure, at a temperature of around 120° C. However, this approach does not provide control over elution of the contrast agent from the bead nor does it contemplate the impact of contrast agent on the loading and elution of drug.

WO2011/110589 describes synthesis of an iodinated poly (vinyl alcohol) by grafting iodobenzoyl chloride to poly (vinyl alcohol) via ester linkages. Whilst this polymer is demonstrated to be radiopaque, it results in a water insoluble polymer, which cannot then be formed into microspheres through the water-in-oil polymersation processes normally used to generate hydrogel microspheres with desirable embolization properties. The same publication mentions microspheres but contains no disclosure as to how this is achieved. The applicants have found that iodinating raw PVA polymers in this way results in an iodinated polymer which cannot be formed into microspheres through water-in-oil polymerization because of the hydrophobic nature of the resulting iodinated polymer.

Mawad et al (Biomacromolecules 2008, 9, 263-268) also describes chemical modification of PVA-based degradable hydrogels in which covalently bound iodine is introduced into the polymer backbone to render the polymer radiopaque. Iodine is introduced by reacting 0.5% of the pendent alcohol groups on PVA with 4-iodobenzoylchloride. The resulting polymer is biodegradable, embolizes via precipitation and is not formed into microspheres There is clearly a need, therefore, for radiopaque embolics which combine the embolization efficiency and reproducibility of embolic beads with the radiopacity of contrast agents, such as ethiodized oils. Radiopacity (or radiodensity) can be quantified according to the Hounsfield scale, a principle which is central to X-ray computed tomography (CT scan) applications. On the Hounsfield scale, distilled water has a value of 0 Hounsfield units (HU), while air is specified as −1000 HU. In addition to good radiopacity, such an embolic bead would ideally have properties which enable efficient load drug loading and elution such that chemoembolization procedures may be monitored with confidence.

The applicants have established that by utilizing relatively straightforward chemistry, it is possible to post-process pre-formed hydrogel microspheres to make them permanently radiopaque, without adversely affecting the physical properties of the microsphere (i.e. size, spherical shape, high water content, swellability, and compressibility) that make them so suited to embolization. The radiopaque microspheres have the same, or better, drug loading and elution properties as the non-radiopaque beads from which they are formed. The radiopacity of the microsphere is also permanent or sufficiently long-lived to allow for monitoring during clinical follow up. The post-processing of pre-formed beads provides a degree of flexibility in terms of manufacturing in that the same manufacturing process can be used for radiopaque and non-radiopaque beads and size selection or sieving can be made prior to post-processing so that only a particular size or size range of beads may be made radiopaque.

Accordingly, in a first aspect, the present invention provides an activated hydrogel bead which has been activated towards nucleophilic substitution reaction with carbonyl diimidazole or carbodiimide. The activated bead is characterized in that a pre-formed hydrogel bead has been activated by reaction with carbonyldiimidazole, an analogue of carbonyldiimidazole or a carbodiimide.

Carbonyldiimidazole and analogues of carbonyldiimidazole are N-Acylimidazoles are well-established reagents which, like carbodiimide, are traditionally used to provide specific and practical conjugation to carboxylic acids, amines and alcohols. Carbodiimides (or methanediimine) comprise a functional group consisting of the formula RN=C=NR. Typical carbodiimides include N,N'-diisopropylcarbodiimide ("DIC"), 1-ethyl-3-(-3-dimethylaminopropyl) carbodiimide hydrochloride, ("EDC" or "EDAC"), N',N'-dicyclohexyl carbodiimide, ("DCC"). Carbonyldiimidazoles are alternative reagents to carbodiimides, which perform a similar function, although they are moisture sensitive. Analogues of carbonyldiimidazole have been reported in the literature, including the carbonylditriazole variant (Beyerman, H. C., *Recl., Trav. Chim. Pays-Bas* (1961) 80, 1372) and other variants (Armstrong, A. In *Encyclopedia of Reagents for Organic Synthesis*, Paquette, L. A., Ed.; Wiley: Chichester, UK, (1995); p1010).

As used herein hydrogel refers to a superabsorbent network of crosslinked hydrophilic polymer chains that are able to absorb extremely large amounts of water relative to their own mass. Hydrogels can contain as much as 99.9% water. Typical hydrogels are polyhydroxy polymers, such as polymers of vinyl alcohols, polyacrylate polymers, such as polyacrylic acid or polymethacrylic acid and copolymers of any of these polymers.

Activation of the hydrogel bead is thought to occur by reaction of pendent carboxylic acid, amine or hydroxyl moieties throughout the loose hydrogel network with activating agents which activate the hydrogel polymer towards nucleophilic attack.

In particular, hydrogel beads made from polyhydroxy polymers such as polyvinyl alcohol (PVA) or copolymers of vinyl alcohol are particularly useful and are readily activated by reaction of pendent hydroxyl moieties with the polymer network with activating agents such as carbonyldiimidazole. Modified PVA hydrogels, with a polymer backbone with a 1,2-diol and/or a 1,3-diol structure are particularly useful because the diol groups crosslink with acrylic and similar monomers to provide high water content, compressible microspheres with good embolization properties. A particularly preferred polymer hydrogel of this type is an acrylamido PVA (polyvinyl alcohol partially acetalized with N-formylmethyl acrylamide) copolymerised with an acrylic monomer, such as 2-acrylamido-2-methylpropane sulfonic acid (AMPS). Such PVA-AMPS hydrogel beads are commercially available (Bead Block®, LC Bead™, DC Bead® Biocompatibles UK Ltd).

The activated beads are made by suspending pre-formed beads in a suitable organic solvent until they have swollen. Polar aprotic solvents, such as dimethyl sulfoxide (DMSO), tetrohydrofuran (THF), ethyl acetate (EtOAc), acetone (CH3—C(=O)—CH3), dimethylformamide (DMF) and acetonitrile (MeCN) are suitable solvents. DMSO is particularly preferred due to its ability to swell hydrogel beads and its miscible in a wide range of organic solvents as well as water. Activating agent, such as carbonyldiimidazole, is then added to the suspension of swollen beads in solvent, in the presence of a catalytic amount of a base and under anhydrous conditions to achieve activation. The base is typically of moderate strength (pKa of conjugate acid around 10-13) and suitable bases will be well known to the organic chemist and will include a variety of pyridines, amines and nitrogen heterocycles, triethylamines, N,N-diisopropylethylamine, DMAP and the like. The reaction is typically conducted under gentle heating (30-80° C.) for 24 hours, although this can be varied to modify reaction times as will be routine in the art. After the reaction is complete, the activated beads may simply be filtered and washed with organic solvent to provide purified activated beads.

The activated beads are stable and are particularly useful because they are susceptible to nucleophilic substitution reactions, which may be used to functionalize the beads in a controlled manner to provide hydrogel beads which have, covalently bound throughout their network, radiopaque materials, such that the entire bead is rendered radiopaque.

Accordingly, in a second aspect the present invention provides a radiopaque hydrogel bead comprising the activated hydrogel bead of any of claims 1 to 5 coupled with an iodinated compound which is reactive towards the imidazole or diimide functionality of the activated bead. The radiopaque hydrogel bead is formed by reaction of the activated hydrogel bead described above with an iodinated organic material. In this way, the beads comprise iodinated compounds, covalently incorporated into the polymer network of the hydrogel bead. Typically, the iodinated material will be an iodinated aryl compound but any iodinated compound which is reactive towards the imidazole or diimide functionality (as appropriate, depending on the activation chemistry selected) of the activated bead is suitable.

Iodinated alcohols, iodinated amines or iodinated carboxylic acids are thus all suitable reactants for rendering the activated beads radiopaque. Iodinated alcohols, and particularly, iodinated aryl alcohols such as triiodobenzyl alcohols or triiodophenyl alcohols are particularly suitable because of the relatively high degree of iodination available whilst retaining a suitable level of reactivity towards the activated bead.

In a particularly preferred embodiment, the radiopaque hydrogel bead is an activated PVA or PVA-AMPS hydrogel as described above coupled with 2,3,5-triiodobenzyl alcohol. Beads modified in this way have good levels of radiopacity while retaining physical properties such as size, compressibility and drug loading efficiency that enables their use in chemoembolization.

The reaction of the activated bead with the iodinated material is particularly useful as it may be carried out in a single reaction vessel, immediately after the activation of the bead, or the activated beads, prepared as described above, may be filtered, washed with solvent and then immediately added to a vessel comprising the iodinated material e.g. triiodobenzyl alcohol, in suitable dry solvent and in the presence of base. As above, the reaction is typically conducted with stirring, under gentle heat (30-80° C.) for 24 hours or less. The resulting radiopaque beads are stable and may be isolated by filtration and washing with solvent. The beads retain hydrogel bead characteristics and reaction solvent may be exchanged for water, upon which the bead absorbs its characteristic high quantity of water or water for injection.

The size of the radiopaque beads prepared according to the second aspect may be controlled by selecting the size or range of sizes of the pre-formed beads which are activated in the initial activation step and the resulting radiopaque bead size, although likely to be smaller, is not significantly changed after reaction. However, if required, a narrower size range may be selected by sieving or selectively filtering the resulting radiopaque beads. In this way, accurately calibrated radiopaque beads are provided which may be used directly in embolization procedures or may be loaded with chemotherapeutic drugs, such as doxorubicin, irinotecan, epirubicin and the like.

It will be understood, however, by the person skilled in the art that, once an activated hydrogel bead has been prepared, a high degree of selectivity is available in a polymer network which was largely unreactive, such that other chemistries may be adopted to tailor and control how radiopaque iodinated compounds may be covalently incorporated into the hydrogel network. For example the activated bead may be further functionalized to enable chemistries beyond those that are available with standard carbodiimide or carbonyldimidazole nucleophilic substitutions. For example, reactive spacers or linker molecules may be grafted onto the activated hydrogel bead, provided they have at least one functionality (i.e. functional group) which is reactive to activated imide or imidazole functionality of the activated bead. The spacer or linker molecule will then have a second functionality that enables further reaction to render the bead radiopaque. The inventors have found this to be particularly useful in tailoring bead chemistry e.g. to account for steric effects which may hinder direct reaction of the activated bead.

Accordingly, in a third aspect, the present invention provides a reactive hydrogel bead comprising the activated hydrogel bead described above and having coupled to its imide or imidazole function, a bifunctional linker which comprises an aliphatic carbon chain with at least 2 carbons. The functional groups of the bifunctional linker are preferably, but not essentially, situated at the terminal ends of the linker. The bifunctional linker is characterized in that one functionalities of the linker must be of the activated bead and, preferably both functionalites are reactive with imide or imidazole to enable further reaction. Thus, the reactive hydrogel bead is formed by simply reacting of the activated hydrogel bead, prepared as described above, with a bifunctional linker which comprises an aliphatic carbon chain with at least 2 carbons wherein both functionalities are reactive with imide and/or imidazole. In a preferred structure, the functionalities of the linker are at terminal ends of the molecule.

In order to retain the ability to use further activation strategies the functionality or reactive moieties of the bifunctional linker conveniently comprises one or more of an amine, carboxylic acid and alcohol. In a preferred embodiment, both moieties are the same and it is particularly preferred that the bifunctional linker is a diamino alkane compound of general formula $H_2N(CH_2)_nNH_2$ wherein n includes any number between 2 and 20. Preferably the number of carbons in the aliphatic carbon chain is between 2 and 10 carbon atoms, ideally between 2 and 4 carbon atoms.

A particular embodiment of the third aspect provides a radiopaque hydrogel bead comprising the reactive hydrogel bead described above and having covalently coupled through its bifunctional linker, an iodinated compound. Conveniently, the radiopaque hydrogel bead is formed by further activation of the reactive hydrogel bead (i.e. the reactive terminal end of the linker which is covalently coupled to the bead) and subsequently reacted with an iodinated compound to render the bead radiopaque. In this way the same activation chemistry may be utilized twice: firstly to activate a pre-formed hydrogel bead towards reaction with a bifunctional linker; and, secondly, to activate the terminal end of the bifunctional linker towards reaction with a iodinated compound. Again it is preferred that the bifunctional linker is an aliphatic diamino alkane linker, such as 1,3-diaminopropane. After activation of the terminal amine, the bead, via its linker, is reactive towards iodinated alcohols, amines or carboxylic acids. In this embodiment it is preferred that the iodinated material is an iodinated benzyl or phenyl alcohol or is an iodinated benzoic acid, such as 2,3,5-triiodobenzoic acid. 2,3,5-triiodobenzoic acid is particularly preferred in this embodiment.

By performing activation chemistry on a relatively unreactive embolic hydrogel bead, the inventors have produced a radiopaque hydrogel bead characterized in that functional groups on a preformed hydrogel bead have been reacted with an iodine containing compound. The iodine containing compound is suitably an iodinated benzyl or phenyl alcohol or is an iodinated benzoic acid, such as 2,3,5-triiodobenzoic acid. The chemistry works particularly well on hydrogel beads which have been pre-formed from crosslinked polyvinyl alcohol. A particular example of such crosslinked PVA is described in WO 2004/071495, which describes a hydrogel bead, formed from a crosslinked polyvinyl alcohol which, itself, has been formed by copolymerizing ethylenically unsaturated polyvinyl alcohol macromer with ethylenically unsaturated comonomer. The macromer comprises pendant ethylenic groups are linked via cyclic acetal linkages with oxygen atoms from adjacent hydroxyl groups, formed by the reaction of N-acrylaminoacetaldehyde dimethyl acetal and the ethylenically unsaturated comonomer is 2-acrylamido-2 methylpropanesulfonate sodium salt. The radiopaque beads as described in this paragraph form a fourth aspect of the invention.

In a fifth aspect, the invention provides a radiopaque hydrogel bead as described above, which comprises a pharmacologically active agent absorbed within the bead. It is preferred that the pharmacologically active bead is an anti-angiogenic or a chemotherapeutic drug, as are well known in the art. Particularly suitable classes of drugs are anthracyclines, such as doxorubicin, daunorubicin, epirubicin and idarubicin, camptothecins and camptothecin analogues such as irinotecan. Other particularly suitable drugs include rapamycin, paclitaxel, ibuprofen, cisplatin, sunitinib, angiostatin Kl-3, arresten, DL-a-difluoromethyl-ornithine, fumagillin, genistein, staurosporine, thalidomide, tumstatin, axitinib, bortezomib, bosutinib gefitinib, pazopanib, semaxanib, sorafenib, vandetanib, vatalanib, canertinib, dovitinib, dasatinib, erlotinib, imatinib, lapatinib, masutinib, mubitinib, lestaurtinib, pazopanib, tandutinib and vismodegib, The radiopaque beads described above are particularly useful in embolization or chemoembolization procedures. Accordingly, in a sixth aspect, the invention provides a method of treatment in which a radiopaque bead as described herein is administered to a patient in order to embolize a solid tumor.

The inherent radiopaque properties of the beads mean that a clinician can image the beads during and after administration with confidence that images are representative of the beads themselves, rather than heterogeneous contrast agent. In a particular embodiment, the radiopaque beads are formulated and administered in a composition which further comprises traditional contrast agent, such as ethiodized oil. This embodiment is advantageous because the combination of two discrete radiopaque materials gives the clinician a further degree of discrimination between the composition and the embolic beads within the composition. Consequently, a further aspect of the invention provides a method of monitoring an embolization procedure by administering radiopaque hydrogel beads as described above into a blood vessel of a patient and detecting presence of the bead in tissue using X-rays.

The invention will now be described by way of example with reference to the following figures, in which.

FIG. 4A shows Clinical CT micrographs of radiopaque beads prepared according to example 5 (A) at 3.1%, 6.2% and 12.5% packed volume of beads. FIG. 4B shoes Micro CT images of 3.1% packed bead volume in agarose phantom. FIG. 4C shows the MicroCT images of the same bead volume in which the bead had been loaded with doxorubicin hydrochloride.

Figure 5:
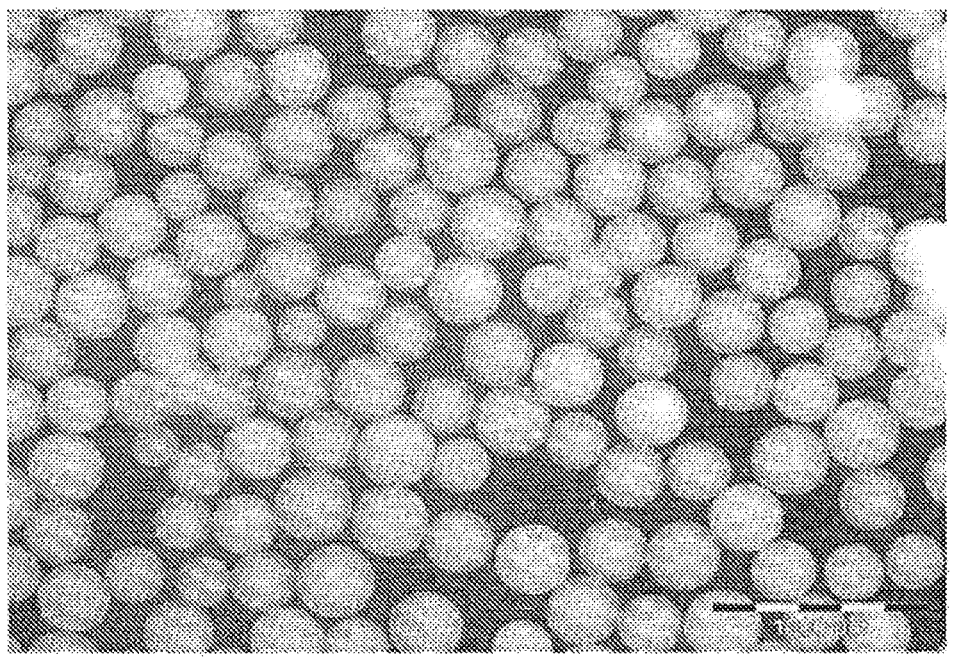

FIG. 5 shows Micrograph of 100-300 µm beads sieved after iodination in accordance with the reaction described in Example 8.

Figure 6:
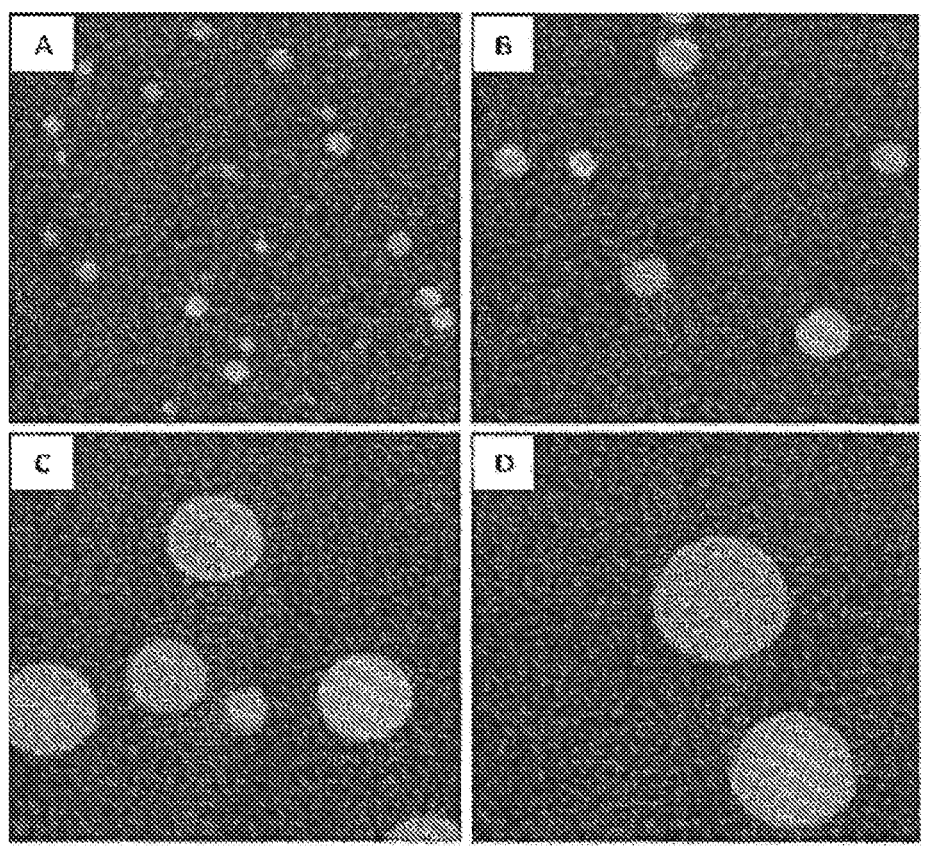

FIG. 6 shows MicroCT images of iodinated beads with size range (A) 70-150 µm, (B) 100-300 µm, (C) 300-500 um, and (D) 500-700 µm, prepared according to Example 8.

MATERIALS AND METHODS USED IN THE EXAMPLES

Materials

Sulphonate modified polyvinyl alcohol AMPS microspheres (LC/DC-Bead™, Biocomaptibles UK Ltd) were prepared as described in Example 1 of WO 2004/071495. Anhydrous dimethyl sulfoxide (DMSO), 1,1'-Carbonyldiimidazol (CDI), 2,3,5-triiodobenzyl alcohol, 2,3,5-Triiodobenzoic acid, N,N'-Diisopropylcarbodiimide (DIC), 1-Hydroxybenzotriazole hydrate (HOBt), 4-(Dimethylamino)pyridine (DMAP), 1,3-Diaminopropane, triethylamine (Et3N), and anhydrous dichloromethane (DCM) were purchased from Sigma Aldrich. Doxorubicin (Dox) was obtained from Bedford Laboratories. De-ionized water (DI water) obtained from Millipore purification system.

General Methods

PVA-AMPS Hydrogel Bead Formation

The first stage of microspheresynthesis involves the preparation of Nelfilcon B—a polymerisable macromer from the widely used water soluble polymer PVA. Mowiol 8-88 poly(vinyl alcohol) (PVA) powder (88% hydrolised, 12% acetate content, average molecular weight about 67,000 D) (150 g) (Clariant, Charlotte, N.C. USA) is added to a 2 litre glass reaction vessel. With gentle stirring, 1000 ml water is added and the stirring. increased to 400 rpm. To ensure complete dissolution of the PVA, the temperature is raised to 99±9° C. for 2-3 hours. On cooling to room temperature N-acryloylaminoacetaldehyde (NAAADA) (Ciba Vision, Germany) (2.49 g or 0.104 mmol/g of PVA) is mixed in to the PVA solution followed by the addition of concentrated hydrochloric acid (100 ml) which catalyzes the addition of the NAAADA to the PVA by transesterification. The reaction proceeds at room temperature for 6-7 hours then stopped by neutralisation to pH 7.4 using 2.5M sodium hydroxide solution. The resulting sodium chloride plus any unreacted NAAADA is removed by diafiltration using a stainless steel Pellicon 2 Mini holder stacked with 0.1 m$^2$ cellulose membranes having a pore size with a molecular weight cut off of 3000 (Millipore Corporation, Bedford, Mass. USA). Upon completion, the macromere solution is concentrated to 20-23% solids with a viscosity of 1700-3400 cP at 25° C.

Hydrogel microspheres are synthesized by suspension polymerization in which an aqueous phase comprising the modified PVA macromer is added to an immiscible organic phase comprising 2-acrylamido-2-methylpropane sulfonic acid (AMPS) and rapidly mixed such that the aqueous phase is dispersed to form droplets, the size and stability of which can be controlled by stirring rates, viscosity, ratio of aqueous/organic phase and the use of stabilizers and surfactants which influence the interfacial energy between the phases. The resulting hydrogel microspheres are recovered by filtration and washing and may be sieved to provide particular size ranges. Unless otherwise stated preformed hydrogel beads were 300-500 µm diameter.

Evaluation of Imageable Beads with Microscopy

The size and appearance of beads during various steps of synthesis and doxorubicin loading were examined and imaged in a chamber slide (Electron Microscopy Sciences; ~150 µl bead and DI water suspension). Bright field images were acquired with a 5× objective on an upright microscope (Zeiss, Axio Imager.M1, Thornwood, N.Y.) equipped with a color CCD camera (Axiovision, Zeiss).

Phantom Preparation

In order to assess radiopacity, beads were suspended in an agarose matrix at bead concentrations (bead volume percent) that is relevant for in vivo applications. Bead containing agarose phantoms (0.5% w/v) with various concentrations (bead volume percents ranging from 0, 3.1, 6.2 and 12.5%) were prepared by adding a 1% agarose mixture to an equal volume of bead suspension in deionsed water. The solutions were mixed while allowing the agarose to slowly gel (over ice), resulting in a homogeneous distribution of beads. The bead volume percent is packed bead volume due to gravity alone and does not account for aqueous solution between the packed beads or altered bead packing efficiency.

In Vitro Evaluation of Imageable Beads with Clinical CT

The distribution of conjugated iodine contrast agent within the radiopaque microspheres was imaged on a clinical 256 Slice CT (Philips, Andover, Mass.) to determine the overall attenuation with the following settings: 465 mAs tube current, 80 keV tube voltage, 1 mm thickness, 0.5 mm overlap. The average attenuation of an 80 mm2 rectangular region in the middle slice of a given phantom was measured using OsiriX.

In Vitro Evaluation of Imageable Beads with Micro-CT

Micro-CT imaging and analysis of imageable bead containing phantoms was performed with a SkyScan 1172 high-resolution micro-CT (Skyscan, Konitch, BE) to evaluate the radiopacity of each individual bead, as well as, intra-bead distribution of iodine. The radiopaque microspheres were imaged at 5 μm resolution, 78 kV, 127 micro-Amps, using a 0.5 mm Aluminum filter. The average attenuation of individual beads was measured and reported as the mean and standard error (n=10).

Example 1: Preparation of Imageable Embolic Beads by Conjugation of 2,3,5-Triiodobenzyl Alcohol on to Preformed PVA-AMPS Hydrogel Embolic Beads

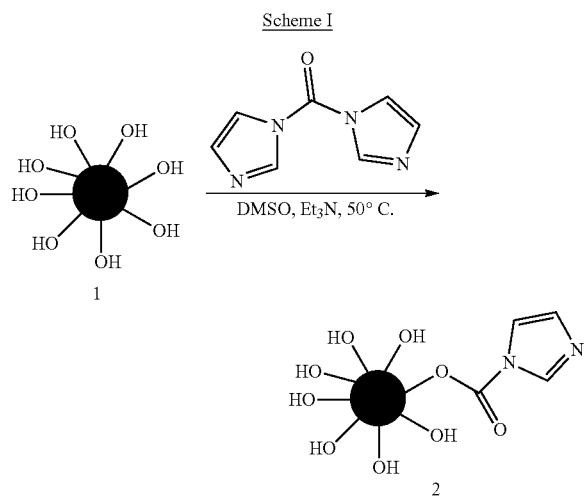

Pre-formed PVA based hydrogel embolic Beads [depicted by Scheme 1, 1] were washed (200 mg) with DMSO (3×5 ml) and the beads were allowed to swell in DMSO (20 ml) for 30 minutes at 50° C. The beads were activated by stirring the suspended beads with carbonyldiimidazole (CDI) (800 mg) (CDI:OH ratio of approximately 1.2:1) in the presence of catalytic amount of triethylamine (0.12 equivalent) at 50° C. for 24 hours to form activated beads (Scheme II). The reaction mixture was cooled to room temperature and washed quickly with a cocktail of DMSO and DCM (1:1) and finally with DMSO alone to provide activated beads [2]. The beads were successfully activated with CDI under very mild conditions. The beads were stored in DMSO for further use.

Example 2: Preparation of Imageable Embolic Beads by Direct Conjugation of 2,3,5-Triiodobenzyl Alcohol to Activated PVA-AMPS Hydrogel Embolic Beads

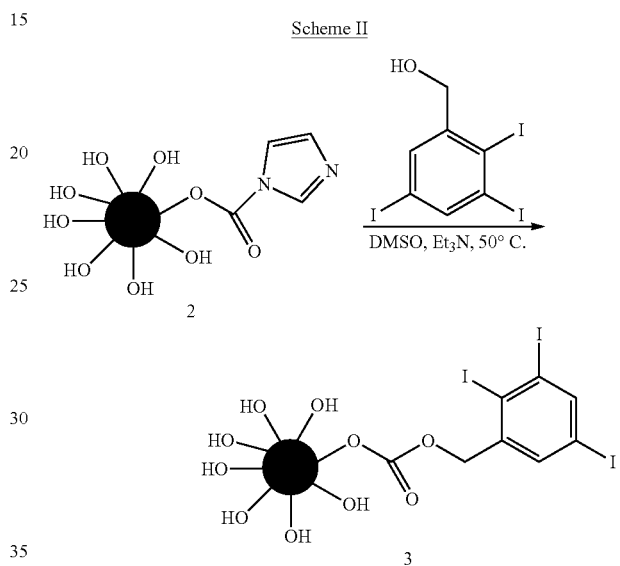

Figure 1A:
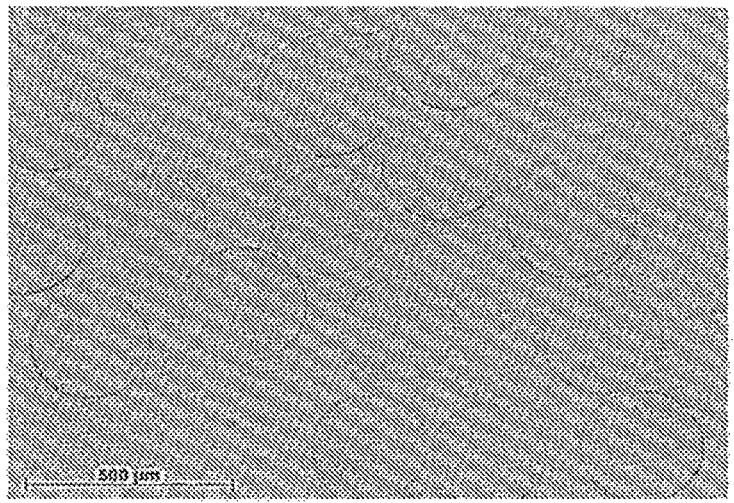
FIG. 1 shows the size and appearance (A) pre-formed hydrogel bead, prior to activation and (B) imageable bead prepared according to the reaction described in Example 2.
Figure 1B:
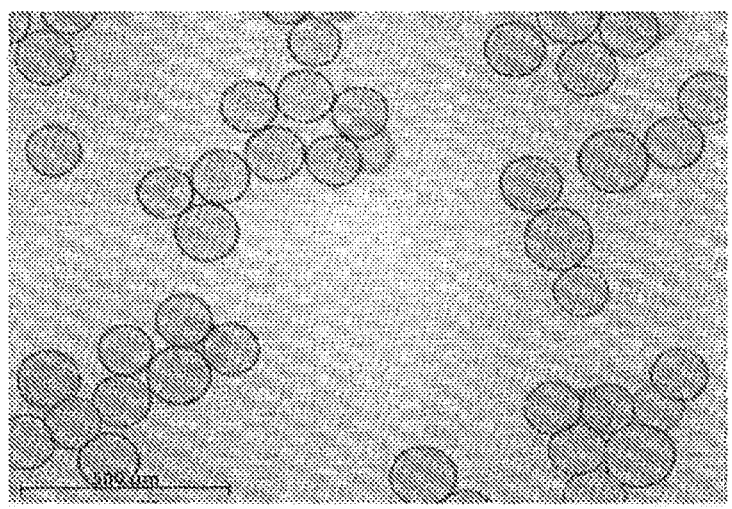
Figure 2A:
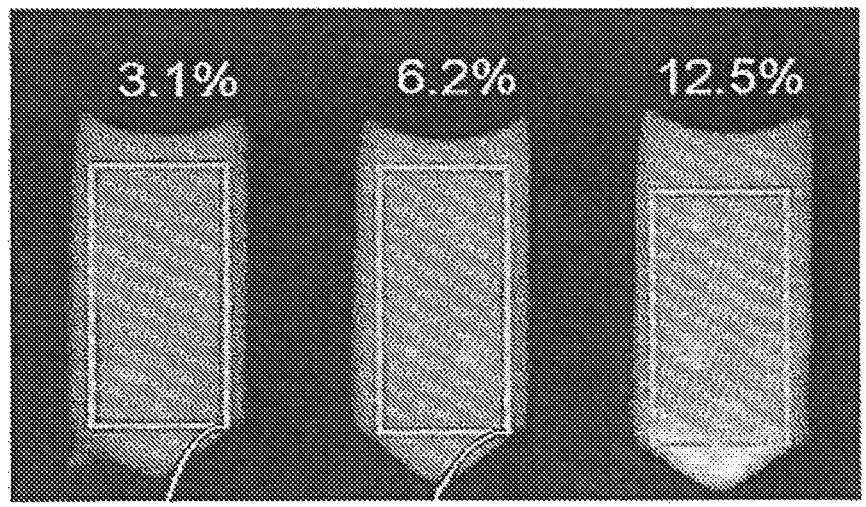
FIG. 2 shows Clinical CT. (A) and Micro CT images (B) of imageable bead prepared according to the reaction of Example 1.
Figure 2B:

Activated beads were prepared according to Example 1. Activated beads were immediately transferred into a reaction flask containing a solution of 2,3,5-Triiodobenzyl alcohol (971.7 mg) in DMSO (10 ml) and stirred for 24 hours at 50° C. (Scheme II). The resulting product cooled to room temperature and was washed thoroughly with DMSO:DCM (1:1), followed by DMSO alone. Finally, the DMSO was exchanged with DI water (under continuous agitation) and the image-able beads thoroughly washed with saline and DI water consecutively. The clean imageable beads were suspended in DI water until further analysis. The beads were successfully conjugated with 2,3,5-triiodobenzyl alcohol (as depicted in Scheme II). Microscopic image comparison of pre-formed hydrogel bead (prior to activation) and 2,3,5-triiodobenzyl alcohol conjugated beads (imageable beads) revealed that the imageable beads size is slightly reduced, as shown in FIG. 1, and the beads may be more easily viewed under light microscopy Example 3—Assessment of the Radiopacity of Imageable Hydrogel Beads The radiopacity of imageable beads prepared according to Example 2 was assessed both in clinical and micro CT and they are visualized in both radiographic techniques. In the clinical CT, visualization is based on radiopacity of the imageable beads in an agarose phantom per a given volume. A 3.1% imageable bead packed volume showed a mean attenuation of 26±15 HU (Hounsfield Units) and increased to 41±16 HU and 74±25 HU as the imageable bead packed volume increased to 6.2 and 12.5%, respectively. In micro CT, a single particle showed a mean attenuation of 952.3±93.9 HU (n=10). Images are shown in FIG. 2.

Example 4: Preparation of an Amino-Reactive Activated Hydrogel Bead

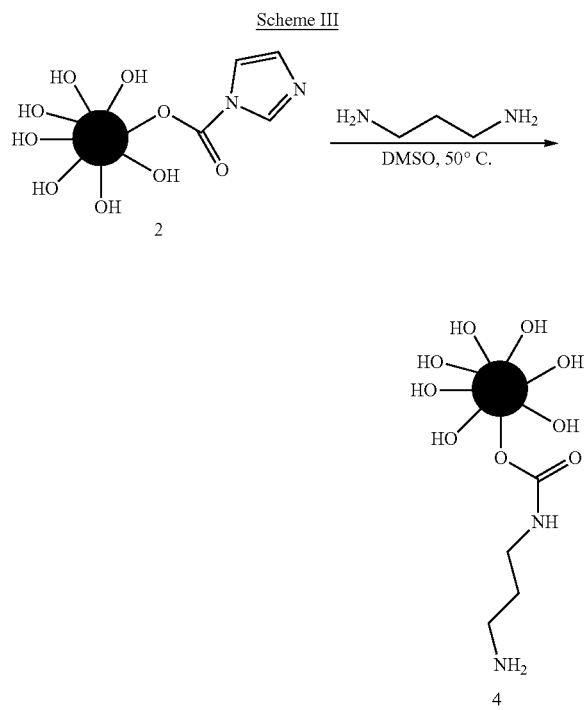

Activated beads, prepared according to Example 1, were reacted with the diamino alkane linker, 1,3-diaminopropane, by mixing at 50° C. for 24 hours (Scheme III). After the reaction was complete, the reaction mixture was cooled and washed thoroughly with DMSO:DCM (1:1), followed by DMSO to yield the amino-reactive hydrogel bead (depicted in Scheme III as [4]). The amino-reactive bead gave a positive ninhydrin response confirming the presence of the terminal primary amine group.

Example 5: Preparation of an Imageable Hydrogel Bead from a Reactive Hydrogel Bead

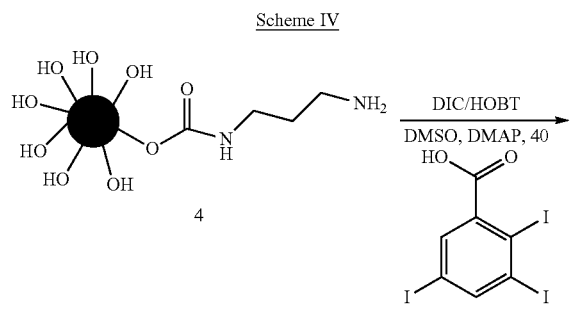

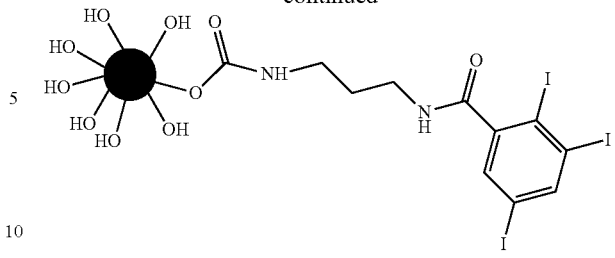

Figure 3A:
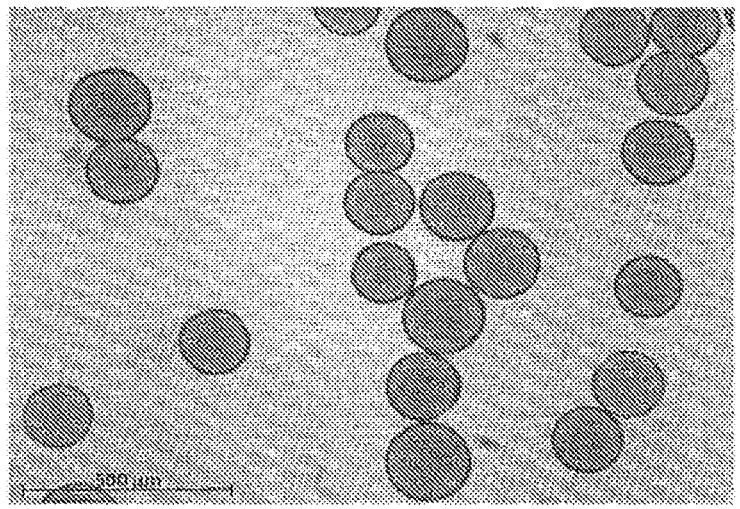
FIG. 3A shows light microscopy image from imageable beads prepared according to Example 5.
Figure 3B:
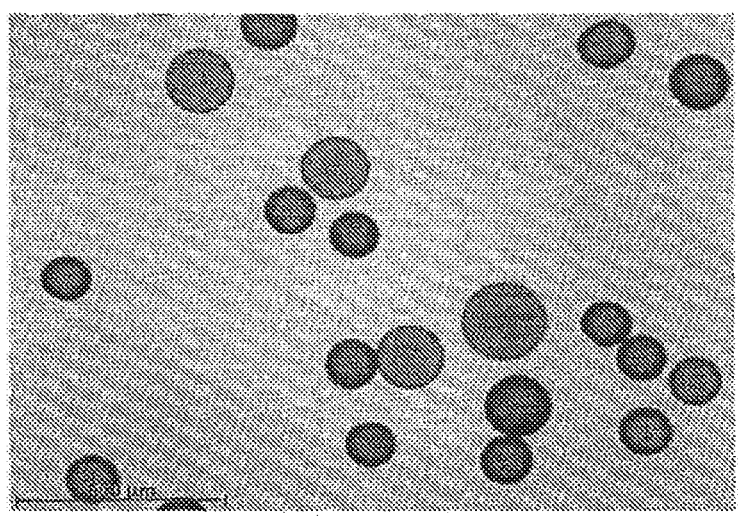
FIG. 3B shows the same beading after loading with doxorubicin as described in Example 6.

A solution of 2,3,5-triiodobenzoic acid (2.4 g) in DMSO (20 ml) was activated with N,N'-Diisopropylcarbodiimide (DIC) (604.5 mg), HOBt (634.2 mg) and DMAP (586.4 mg) for 30 minutes at room temperature and the amino-reactive beads prepared in Example 4 [4] were added (Scheme IV). The resulting reaction mixture was stirred at 40° C. for 3 days. After cooling, the imageable beads [5] were thoroughly washed with DMSO/DCM and DMSO and then finally the solvent was exchanged with deionized water. A light microscopy image of the radiopaque beads in shown in FIG. 3.

Example 6: Doxorubicin Loading into Imageable Beads

Imageable beads, prepared according to Example 5, were loaded with Doxorubicin according to previously reported method (Lewis, A. L. et al. *Journal of Materials Science-Materials in Medicine* 2007, 18, 1691). Briefly, 250 µl of thoroughly washed beads with DI water was immersed into 0.5 ml of Dox (20 mg/ml) solution and shaken for 3 hrs at room temperature. As can be seen from the light microscopy image in FIG. 3B, the doxorubicin loaded radiopaque beads have taken on the characteristic red appearance of doxorubicin loaded hydrogels and appear to have decreased slightly in size.

Example 7: Radiopacity of Imageable and Drug-Loaded Imageable Beads

The radiopacity, or radiodensity, of the beads prepared in Examples 6 and 7 were assessed in clinical and micro CT with both techniques confirming that both sets of beads are radiopaque and easily visualized in both radiographic techniques. In the clinical CT, visualization is based on radiopacity of the beads per given volume. A 3.1% packed bead volume showed a mean radiopacity of 129±33 HU and increased to 269±53 HU and 444±83 HU as the bead packed volume increased to 6.2 and 12.5%, respectively. This is shown in FIG. 4A. In micro CT, individual "bland" and Doxorubicin loaded beads showed a mean attenuation of 7903.99±804 HU (n=10) and 11873.96±706.12, respectively. These are shown in FIGS. 4B and 4C, respectively.

Example 8: Preparation of Radiopaque Hydrogel Beads by Activation of Iodinated Benzoic Acid In a reaction vessel, 10 g of acetone-dried PVA beads were mixed with 200 mL of anhydrous DMSO by stirring for 30 min at 50° C. Subsequently 41.6 g of 1,1'-carbonyldiimidazole (CDI) and 4.1 mL of triethylamine were added into the bead suspension under a nitrogen blanket. After the reaction was complete, the temperature was reduced to room temperature, approximately 22° C. Then 200 ml of anhydrous diethyl ether was added into the reaction mixture and stirred over 10 min, followed by removal of the solvents. The activated beads were then washed with mixed solvent of DMSO and diethyl ether (1:1, v/v) three times. Elemental analysis of the activated beads confirmed that conversion of OH by CDI activation was approximately 30%.

A bifunctional linker was then grafted on to the activated beads. Activated beads were suspended in 200 ml of anhydrous DMSO at 50° C., and 18.5 g of 1,3-diaminopropane was added into the bead suspension. After the reaction was complete, the reaction vessel was cooled down to room temperature and the resulting beads were washed by diethyl ether and DMSO mixture three times, followed by the removal of solvents.

In a final step, triiodobenzoic acid was activated towards reaction with the activated bead; In a round bottom flask 40 g of 2,3,5-triiodobenzoic acid (TIBA), (a concentration equivalent to ⅓ of initial OH on beads), was dissolved in 100 ml of anhydrous DMSO. The compound was then activated by adding 13 g of CDI powder, resulting in a steady release of $CO_2$ (at room temperature), the solution becoming turbid and viscous after stirring for about 30 to 60 min. The mixture was then added into a suspension of activated beads in 100 ml of DMSO. At 50° C., the suspension was stirred for over 24 hr whilst protected from light. Finally, the beads were washed with diethyl ether and DMSO mixture and deionized water.

A light micrograph image of the resulting beads, after sieving, is shown in FIG. 5. MicroCT image of bead phantoms is shown in FIG. 6. The iodine content of vacuum-dried beads was 42-45% by elemental analysis. Table 1 shows the measured bead solid content, iodine content and parameters of characterization.

Example 9: Effect of Temperature on Activation Chemistry

As a comparison, this example conforms in all respects to Example 8, except that a reaction temperature of 70° C. was used in all three steps and ⅔ of TIBA equivalent to initial OH on beads are used in the third step. The beads appeared more brown color under these higher temperature conditions. The iodine content of dried beads is listed in Table 1, indicating slightly less conjugation efficiency. The beads were further autoclaved under 121° C. for 20 min, and no damage/degradation was observed post-sterilisation.

Example 10: Drug-Loading Efficiency of Radiopaque Beads

Drug loading capacity of the beads prepared according to Example 9 was tested by adding 2.87 ml of doxorubicin solution (24.4 mg/ml) to 1 ml of beads (sieved, 100-300 μm) with occasional agitation. After 24 hr, the residual doxorubicin in solution was measured by UV at 483 nm, and the loading yield was calculated as 99.6%.

Example 11: Carbodiimide Coupling of Beads

This example is the same in all respects as Example 9, other than that in the third step, an alternative coupling agent, N,N'-diisopropylcarbodiimide (DIC) was used in the reaction of TIBA and reactive (amino-linked) beads. Equivalent DIC and TIBA to initial OH on beads were used in this case. The iodine content of final dried beads was confirmed by elemental analysis to be 17.7%, illustrating a lower conjugation efficiency that that observed in Examples 8 & 9.

TABLE 1

Iodine Content and Radiodensity of Radiopaque beads prepared according to the Examples 8 and 9

| Example No./ bead size (μm) | | Solid content (%) | Iodine content (%) | MicroCT Attenuation (HU) |
|---|---|---|---|---|
| 4 | 70-150 μm | 27.2 | 41.9 | 9758 ± 1476 |
|   | 100-300 μm | 24.8 | 44.3 | 8037 ± 1142 |
|   | 300-500 μm | 23.7 | 45.1 | 8243 ± 1240 |
|   | 500-700 μm | 23.0 | 45.6 | 7326 ± 773 |
| 5 | 70-150 μm | 37.8 | 32.4 | — |
|   | 100-300 μm | 34.1 | 38.5 | — |
|   | 300-500 μm | 32.0 | 40.1 | — |

The invention claimed is:

1. A method of making a radiopaque hydrogel bead, comprising:
forming an activated hydrogel bead by reacting a preformed hydrogel bead with a carbonyldiimidazole or a carbodiimide; and
reacting functional groups on the activated hydrogel bead with an iodinated compound such at the iodinated compound is covalently coupled to the activated hydrogel bead, wherein the iodinated compound is an aromatic iodine containing compound.

2. The method according to claim 1, wherein the aromatic iodine containing compound is an iodinated benzyl or phenyl alcohol or is an iodinated benzoic acid.

3. The method according to claim 1, wherein the aromatic iodine containing compound is 2,3,5-triiodobenzoic acid.

4. The method according to claim 1, comprising preforming the preformed hydrogel bead from a polymer which has alcoholic hydroxyl substituents or acylated derivatives thereof.

5. The method according to claim 1, wherein the preformed hydrogel bead comprises a cross-linked polyhydroxy polymer selected from polyvinyl alcohol (PVA) or a copolymer of vinyl alcohol.

6. The method according to claim 1, wherein the preformed hydrogel bead comprises a polymer backbone with a 1,2-diol and/or a 1,3-diol structure to enable crosslinking with an acrylic monomer.

7. The method according to claim 6, wherein the acrylic monomer is 2-acrylamido-2-methylpropane sulfonic acid (AMPS).

8. The method according to claim 1, wherein hydroxyl moieties on and/or within the preformed hydrogel bead are activated by reaction with the carbonyldiimidazole.

9. The method according to claim 1, wherein the iodinated compound is an iodinated alcohol, an iodinated amine, or an iodinated carboxylic acid.

10. The method according to claim 1, wherein the iodinated compound is an iodinated alcohol.

11. The method according to claim 10, wherein the iodinated alcohol is a triiodobenzyl alcohol or a triiodophenyl alcohol.

12. The method according to claim 1, having coupled to its imide or imidazole function, a terminally bifunctional linker which comprises an aliphatic carbon chain with at least 2 carbons.

13. The method according to claim 12, wherein both functionalities of the terminally bifunctional linker are reactive with imide or imidazole.

14. The method according to claim 12, wherein the functionality or reactive moieties of the bifunctional linker comprise one or more of an amine, carboxylic acid and alcohol.

15. The method according to claim 12, wherein the bifunctional linker is a diamino alkane, optionally wherein bifunctional linker has general formula $H_2N(CH_2)_n NH_2$ wherein n includes any number between 2 and 20, 2 and 10, or 2 and 4.

16. The method according to claim 12 wherein the iodinated compound is covalently coupled through the bifunctional linker.

17. The method according to claim 1, further comprising absorbing a pharmacologically active agent within the radiopaque hydrogel bead.

18. The method according to claim 1, comprising:
adding the carbonyldiimidazole or the carbodiimide to a suspension that contains the preformed hydrogel bead, wherein the preformed hydrogel bead is swollen with an organic solvent, in the presence of a catalytic amount of a base and under anhydrous conditions to react with the preformed hydrogel bead such that it is activated towards nucleophilic substitution; and
covalently coupling the activated hydrogel bead with the iodinated compound which is reactive towards the imidazole or diimide functionality of the activated hydrogel bead.

19. The method according to claim 18, wherein the preformed hydrogel bead comprises a cross-linked polyhydroxy polymer selected from polyvinyl alcohol (PVA) or a copolymer of vinyl alcohol.

* * * * *